United States Patent [19]

Lukens

[11] Patent Number: 4,590,377

[45] Date of Patent: May 20, 1986

[54] IN SITU ISOTOPIC MEAT GRADER

[75] Inventor: H. Richard Lukens, La Jolla, Calif.

[73] Assignee: IRT Corporation, San Diego, Calif.

[21] Appl. No.: 619,056

[22] Filed: Jun. 11, 1984

[51] Int. Cl.$^4$ .................... G01T 1/167; G01T 1/202
[52] U.S. Cl. .............................. 250/361 R; 250/358.1; 250/362
[58] Field of Search ............... 250/361 R, 362, 363 R, 250/358.1; 209/576, 589

[56] References Cited

U.S. PATENT DOCUMENTS

| | | | |
|---|---|---|---|
| Re. 25,634 | 9/1964 | Pringle et al. | 250/361 R |
| 2,727,154 | 12/1955 | Goldsworthy | 250/367 |
| 2,768,308 | 10/1956 | Schultz | 250/357 X |
| 2,902,603 | 9/1959 | Ferre | 250/368 |
| 2,931,905 | 4/1960 | Caha et al. | 250/368 |
| 2,949,534 | 8/1960 | Youmans | 250/368 X |
| 3,138,709 | 6/1964 | Cassen et al. | 250/367 |
| 3,163,756 | 12/1964 | Meeder et al. | 250/328 |
| 3,237,765 | 3/1966 | Gaudin et al. | 209/111.5 |
| 3,376,417 | 4/1968 | Keck et al. | 250/367 |
| 3,539,806 | 11/1970 | Humphrey | 250/367 X |
| 3,626,183 | 12/1971 | Berry et al. | 250/363 R |
| 3,843,887 | 10/1974 | Morrison | 250/358.1 X |
| 3,883,742 | 5/1975 | Olson et al. | 250/328 |
| 3,898,457 | 8/1975 | Packard et al. | 250/367 X |
| 3,911,271 | 10/1975 | Mitchell | 250/252 |
| 3,944,833 | 3/1976 | Hounsfield | 250/367 |
| 3,946,231 | 3/1976 | Frank | 250/328 |
| 4,263,098 | 4/1981 | Kasperek et al. | 176/10 |
| 4,267,446 | 5/1981 | Brown et al. | 250/255 |
| 4,278,885 | 7/1981 | Von Alftham et al. | 250/358.1 X |
| 4,414,472 | 11/1983 | Watt | 250/359.1 |

OTHER PUBLICATIONS

Pringle Derek H. and Roman Kulwich, "K$^{40}$ Gammas Give Estimate of Lean Meat Content", Nucleonics, Feb. 1961, pp. 74, 76 and 78.

Anon., "Process Analyser with Probe for Potash Content Determination in Raw Salts", *Monthly Technical Review*, vol. 20, No. 10 (Oct. 1976) p. 210.

C. Harwood, K. Walanski, and R. Semmler, "A Miniature Scintillation Probe for Use in Powder Tracer Studies", *Chemical Instrumentation*, vol. 6, No. 3 (1975) pp. 227-237.

A. C. Morris, Jr., T. R. Barclay, R. Tanida and J. V. Nemcek, "A Miniaturized Probe for Detecting Radioactivity at Thyroid Surgery", *Phys. Med. Biol.*, vol. 16, No. 3 (1971) pp. 397-404.

*Primary Examiner*—Alfred E. Smith
*Assistant Examiner*—Constantine Hannaher
*Attorney, Agent, or Firm*—Fitch, Even, Tabin & Flannery

[57] ABSTRACT

A meat grader grades meat disposed in a bin of predetermined dimensions wherein the meat extends at least about two feet in all directions. A probe includes a housing containing a scintillation phosphor responsive to gamma rays including 1.46 Mev gamma rays from potassium-40 for producing corresponding light pulses of magnitude systematically related to the energy of the incident gamma rays, and a photomultiplier optically coupled to the phosphor for producing corresponding electronic pulses of magnitude systematically related to the magnitude of said light pulse. The probe is inserted into the meat to dispose the phosphor near the center of the meat. A differential pulse height discriminator selectively responds to such of the electronic pulses as are of a limited range of magnitude including that characteristic of the 1.46 Mev gamma rays by producing corresponding discriminated signal pulses. A counting rate meter counts the number of said discriminated signal pulses in a predetermined time interval to provide a signal indicating gross counting rate. A background counting rate corresponds to the number of discriminated signal pulses in the predetermined period of time occurring with the probe in a corresponding standard environment in the absence of potassium-40. The background counting rate is subtracted from the gross counting rate to indicate net counting rate corresponding to 1.46 Mev gamma rays from potassium-40. Net counting rate is converted into an indication of the relative leanness or protein content of the meat sample.

16 Claims, 4 Drawing Figures

4,590,377

IN SITU ISOTOPIC MEAT GRADER

BACKGROUND OF THE INVENTION

The present invention relates to the determination of the leanness of meat and more particularly to the determination of the leanness of meat from the relative abundance of gamma rays naturally emitted by the potassium-40 naturally found in lean meat.

It is well known that lean meat contains potassium. Potassium is found in protein but not in fat, and the determination of relative potassium content is indicative of the relative leanness and relative protein content of meat. A determination of relative potassium content therefore provides a method of grading meat.

One way of determining relative potassium content is to determine the relative number of gamma rays emitted by potassium-40, a naturally radioactive isotope of potassium constituting a known portion of naturally occurring potassium. Such gamma rays have a characteristic energy of 1.46 Mev. It is well known to utilize scintillation counters with differential pulse height analyzers to provide a measure of relative potassium-40 content and hence leanness of meat. See, for example, Pringle, Derek H., et al., "$K^{40}$ Gammas Give Estimate of Lean Meat Content," Nucleonics, February 1961, pp. 74-78. In the Pringle et al., device, samples of meat were inserted in the well of a scintillation counter arrangement heavily shielded with lead. Only small samples could be inserted in the scintillation counter well which acted as a 4 pi measuring device.

Another 4 pi measuring device for measuring potassium-40 gamma rays, used for measuring leanness of beef on the hoof, is that shown in Keck, Charles R., et al., U.S. Pat. No. 3,376,417, which disclosed a massive array of heavily shielded scintillation counters in which array an entire animal was confined.

The cost of these massive 4 pi measuring devices heavily shielded on the outside has severely limited their use. According to the present invention no external shielding is required, and a simple probe is inserted into approximately the center of a bin of meat. The meat itself acts to shield the detector from ambient radiation, such as cosmic rays.

In the use of scintillation counters in well logging the earth shielded the detector from the effect of cosmic rays. However, this was not used in measurement of finite samples. See, for example, Youmans, A. H., U.S. Pat. No. 2,949,534. Probes have been used for placing scintillation crystals near the material being measured, as shown in Caha, A., et al., U.S. Pat. No. 2,931,905. However, this was simply to place the detector near the object to be measured, not to place the detector in the center of an object to be measured while utilizing the object being measured as a shield.

SUMMARY OF THE INVENTION

A system in accordance with the invention has been devised and tested for measuring the lean, fat, and/or protein content of large samples of meat. The measurement equipment includes one or more penetrator probes, each of which houses a detector of gamma rays, and electronic equipment with energy discrimination windows for the selective measurement of potassium-40-initiated pulses from the detector or detectors. Each probe has a tapered end to facilitate insertion into meat.

The procedure for measurement of lean, fat, and/or protein is as follows:

1. The measurement equipment is set to measure potassium-40 gamma rays selectively.
2. The probe is inserted into the center of a large sample (approximately one ton) of ground or chunk meat.
3. Potassium-40 gamma ray emissions from the sample are counted for a sufficient period to obtain a statistically useful value of the gross count rate.
4. The foregoing steps may be repeated with an equal volume of water in a container similar to the one used to contain the meat in order to obtain a measure of the background count rate, which may then be subtracted from the measured sample count to provide a net sample count.
5. The net count rate data are converted to lean, fat, and/or protein values by the use of calibration curves. The calibration curves are obtained by counting samples of meat with various and known lean, fat, and protein contents obtained by accurate chemical analyses on representative portions of the large samples of meat. The calibration curve may be mathematically represented and interpreted with the aid of a data processor.

The present invention is particularly adapted for the grading of meat in a packinghouse. It is standard practice in packing houses to place meat in bins of a standard size, notably 4 ft. by 3 ft. by 3 ft., which contain when full about 1 ton of meat. In accordance with the present invention a probe containing a scintillation counter is utilized to place a scintillation phosphor deep in the bin of meat, preferably substantially in the center and leaving at least about one foot of meat surrounding the scintillation phosphor in all directions and hence is an internal 4 pi measurement. This provides a foot of shielding material for shielding the phosphor from the effects of cosmic rays and other background radiation. The probe may be in the form of a housing containing a scintillation phosphor responsive to gamma rays including 1.46 Mev gamma rays from potassium-40 for producing corresponding light pulses of magnitudes systematically related to the energy of the incident gamma rays. The probe housing also contains a photomultiplier optically coupled to the phosphor and responsive to the light pulses for producing corresponding electronic pulses of magnitude systematically related to the magnitudes of the light pulses. The probe housing preferably has a sharp pointed end for penetrating the meat, and the housing is of such size that when the probe is fully inserted the phosphor is disposed near the center of the meat. A pulse height discriminator selectively responds to the electronic pulses in the range corresponding to pulses characteristic of those occasioned by the incidence of the 1.46 Mev gamma rays. A counting rate meter counts the pulses occurring in a predetermined interval and then background counts are subtracted to provide a measure of the net count indicative of the relative presence of potassium and hence the relative leanness or protein content of the meat. The background count may be derived by inserting the probe in a standard environment, such as a tub of water of dimensions comparable to those of the meat, water being about the same density as meat and thus measuring background count in a comparable environment in the absence of potassium.

Normally the bins contain a standard amount of meat, notably about 2000 pounds. However, on occasion the bins are not entirely full. The short weight provides some fewer potassium-40 gamma rays, however the principal effect is to reduce the shielding. Thus, should the weight be very short, some account must be taken of the increased count occasioned by the higher background. In accordance with the present invention this may be done by simply weighing the meat in the bin and making an appropriate adjustment in the determined background count.

A principal aspect of the present invention is thus to provide a meat grader utilizing a scintillation counter and spectral analysis to identify the relative presence of potassium-40 utilizing a probe inserted in the center of a mass of meat which thus provides self-shielding for the measurements. Another aspect of the invention is to provide calibration for such instruments and compensation for background. Another aspect is to provide compensation for short weight. Other objects, aspects and advantages of the present invention will become apparent from the following detailed description, particularly when taken in conjunction with the accompanying drawings.

DETAILED DESCRIPTION

Figure 1:
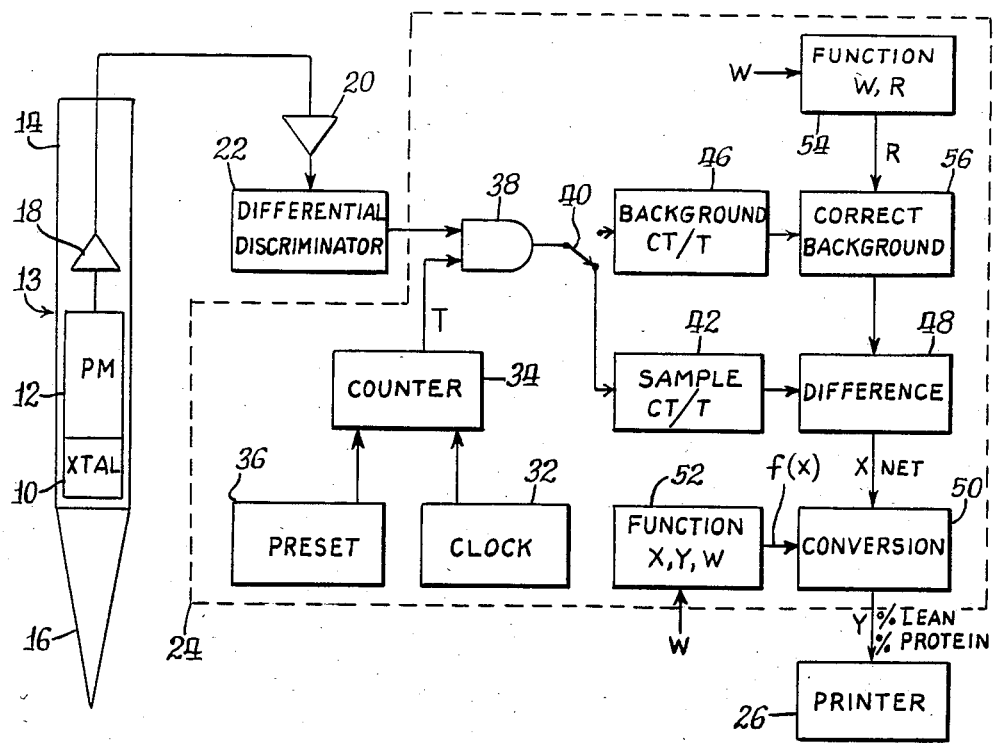
FIG. 1 is an illustration, mostly diagrammatic, of an isotopic meat grader according to the present invention.
Figure 2:
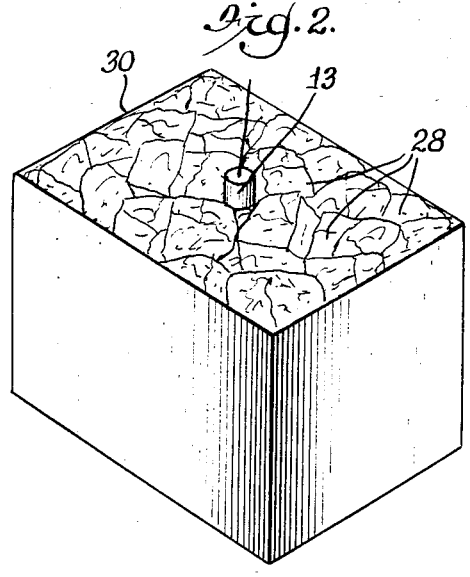
FIG. 2 is an isometric drawing of the probe of the system shown in FIG. 1 as positioned in a sample of meat being measured.
Figure 3:
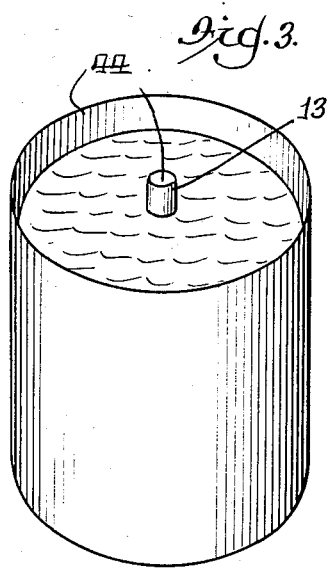
FIG. 3 is an isometric drawing of the probe of the system shown in FIG. 1 as positioned in a standard environment.

As shown in FIG. 1, a 3 in. diameter by 3 in. long thallium activated sodium iodide scintillation crystal 10 optically coupled to a 3 in. diameter and window photomultiplier tube 12 is housed in a probe 13 having a 4 in. diameter by 21 in. stainless steel housing 14 with a 10 in. long, tapered, solid stainless-steel penetrator 16 attached to the housing 14. The crystal 10 is positioned adjacent to the tapered penetrator 16.

The photomultiplier tube is electronically coupled to a battery-powered pulse counting instrument comprised of a high voltage supply (not shown) to the photomultiplier tube 12, a preamplifier 18 adjacent the photomultiplier, an amplifier 20, an adjustable window differential discriminator 22 for selection of photomultiplier pulse heights, data processing means 24 for recording the counts during a preset measurement interval and for data reduction, and a printer 26 for providing a printed record of the measurement results.

Data are acquired by inserting the probe 13 into a meat sample 28 contained in a standard bin 30, which may be 4 feet long, 3 feet wide and 3 feet deep. The bin 30 is preferably substantially filled with meat to provide samples 28 of substantially constant shape and mass, weighing a bit more than 2000 pounds. The probe 13 is inserted with the aid of the penetrator 16 to where the crystal 10 is approximately centered in the sample 28, the probe being of such length that the crystal is centered when the top of the probe is on inch or two above the top of the meat. The penetrator 16 is long enough to prevent the probe 13 from going too far through the sample. This assures 4 pi receipt of gamma rays in substantially equal portions from all directions and assures relatively uniform 4 pi shielding from background radiation.

As is well known, scintillation counters are useful in making spectral measurements of gamma rays. They are, thus, useful in selectively measuring gamma rays characteristic of potassium-40 and, hence, characteristic of the relative presence of protein or lean meat in meat samples, inasmuch as protein contains a characteristic relative amount of potassium, whereas, the remainder of the meat contains relatively none.

In scintillation counters the phosphor or scintillation crystal is responsive to gamma rays and other radiation by producing corresponding light pulses of magnitude systematically related to the energy of the incident radiation. In respect to gamma rays, the phosphor 10 responds to a gamma ray by emitting a photoelectron which moves through the phosphor with the energy of the incident gamma ray, transferring its energy to other electrons as it moves, resulting in the emission of a light pulse of magnitude proportional to the energy of the incident gamma ray, provided the photoelectron (or any secondary electron) does not escape from the phosphor before losing all its energy. Such escape is made relatively negligible by utilizing a relatively large crystal, 3 in. by 3 in. being relatively large for assuring stopping photoelectrons occasioned by 1.46 Mev gamma rays, which are characteristic of potassium-40.

The light pulses from the phosphor are optically coupled to the photomultiplier 12 in such manner as to recover as much of the light as reasonably possible so that the amplitude of the light pulses as received at the photosurface of the photomultiplier are reasonably characteristic of the light pulses as originally generated in the phosphor. The light pulses as received at the photocathode of the photomultiplier 12 are thereby converted into corresponding electronic pulses of magnitude systematically related to the amplitude of the incident light pulses. The electron multiplier section of the photomultiplier amplifies the electronic pulses. The amplified pulses are further amplified by the preamplifier 18 and the amplifier 20 to provide corresponding electronic pulses of magnitude systematically related (substantially proportionally related except for certain losses and statistical variations) to the magnitude of the light pulses and hence the energy of the respective incident gamma rays.

The differential discriminator 22 includes adjustable bias for establishing threshold pulse heights. The discriminator 22 outputs a pulse of uniform height for each input pulse of magnitude between two threshold levels. Input pulses outside this range are ignored. The acceptance range includes pulses characteristic of those produced upon the incidence of 1.46 Mev gamma rays upon the phosphor. This will, thus, include the gamma rays from potassium-40 in the lean meat. Unfortunately, this also includes pulses occasioned by such other radiation as produce electronic pulses in the same range. This includes ambient background radiation, as from cosmic rays, that have not been shielded out by the meat.

Of course, leanness is not determined simply by counting gamma rays. It is their rate that is significant. To this end, the data processor 24 includes timing means comprising a clock 32, a counter 34, a preset circuit 36 and a gate 38. The counter 34 counts timing pulses from the clock 32, which may produce pulses at the rate of 60 Hz. The preset circuit 36 provides a beginning count to the counter 34, which counts until it overflows. The counter 34 provides an output signal T from the time it is enabled by the preset circuit until it overflows. The preset circuit may set this to take, for example, 200 clock cycles. The output signal T would then be 200 seconds long. The output signal T thus enables the gate 38 for 200 seconds, so that the output pulses from the differential discriminator 22 are passed for 200 seconds.

The passed pulses are applied through a switch 40 to a sample counting circuit 42 which acts to count the number of pulses passed by the gate 38 in the time T and is reset to zero before each count. It is possible to count over several intervals T and test the variance between counts as a check for accuracy.

As noted above, the system is sensitive not only to gamma rays from potassium-40 in the meat but also background radiation producing electronic pulses within the discriminator window. To account for the effect of such background radiation, such background radiation may be measured by disposing the probe in a standard environment comparable to the sample measuring environment but having substantially no potassium. Conveniently this is achieved by disposing the probes in a tub 44 of water, the tub having comparable dimensions to those of the bin 30. A tub 44 of 41.5 inches inside diameter containing three feet of water has proven satisfactory, water having substantially the same density as meat. A measurement is made as in measuring a sample, except that the switch 40 is switched to output the pulses to a background counter 46. The background count signal in the background counter 46 can then be differentially combined in a difference circuit 48 with (subtracted from) the sample count signal in the sample counter 42 to provide an indication of net count.

The net count may be converted to a percent by weight (%w) lean or percent by weight protein indication by suitable conversion tables. The conversion tables may be developed empirically by taking test measurements in meat for which the percent lean and/or percent protein have been determined analytically. The conversion table or algorithm may be placed in a conversion circuit 50, as by look up tables in a PROM or by appropriate conventional addition and multiplication circuits. The conversion parameters may be developed from empirical measurements by a function generator 52 as will be discussed further below. The function generator 52 may take data points for net counting rate (X) and percent lean or percent protein (Y) and provide a calibration function $y=f(x)$, as by least squares fitting.

The apparatus and method as thus far described has proven effective in determining percent lean or percent protein, provided the standard environment furnished by the tub 44 is truly comparable to the bin 30 of meat 28 except for the potassium-40. This is generally the case where the meat 28 substantially completely fills the bin and hence provides a standard mass of meat 28 around the probe 13. Where there is short weight, two changes are effected. First, there is less shielding and, hence, a higher background count detected by the crystal 10. Second, there is less meat 28 and, hence, less potassium-40, resulting in a lower count. The latter is partly offset by the fact that the missing meat is that farther from the crystal and, hence, most shielded by the intervening meat anyway.

To account for the added background, a correction factor (R) may be developed as a function of weight (W) and used to correct the background count. This correction factor (R) may be developed empirically by taking test measurements for different background conditions and different standard environments. A conversion table or algorithm may be developed in and/or by a function generator 54 which provides an output R for any input weight W. Thereafter, the meat 28 can be weighed and a signal indicating weight W entered manually or automatically in the function generator 54 to provide the appropriate ratio R for the meat sample being tested. This ratio R is applied to a correction circuit 56 which acts to multiply the background count from the background counter 46 by the ratio R to provide a corrected background count to the difference circuit 48.

Particularly because the background count much exceeds the net sample count, the effect of short weight on the detected potassium-40 gamma rays from the meat is much less than the effect on background and can often be ignored without exceeding the desired limits of accuracy. However, should it be desirable to acount for the decrease in counting rate occasioned by short weight, the function generator 52 may be programmed empirically to provide different functions f(x) for different weights. Then the weight signal W may be applied to the function generator 52 to provide the appropriate function f(x) for that weight.

A signal indicating net count is applied from the difference circuit 48 to the conversion circuit 50, to which the function generator 52 applies the appropriate function f(x). The conversion circuit 50 thereupon converts counting rate to a signal indicating percent by weight lean or percent by weight protein according to the function f(x). The converted signal is then recorded on the printer 26.

The system was tested as described below Boned meat (pork) samples 28 were contained in 4 ft. by 3 ft. by 3 ft. high stainless steel bins 30. Most meat samples weighed slightly more than 2000 pounds and evenly filled the respective bins to the top. A few lightweight samples (under 2000 pounds) were also measured. A 41.5 in. inside diameter by 42 in. high tub 44 was filled to within 6 inches of the top with water and was used for background measurements.

Nine samples of meat in excess of 2000 pounds and four samples under 2000 pounds were counted for 20 minutes each. The background was counted for 20 minutes between each meat measurement. The measurements were spread over three days. Each 20 minute counting interval was comprised of six counting intervals of 200 seconds in order to permit statistical tests on the correctness of the equipment performance. The statistical tests found no intervals of spurious performance, and, thus, the average counts per 200 seconds included all six 200 second counts in every case. The background measurements were sufficiently uniform throughout each day to permit a single average of all measurements throughout the day to be used.

Approximately 5 pounds of meat were taken from each sample by multiple core sampling, ground to a consistency of paste, and small amounts (several grams, weighed) analysed for fat and protein. Fat was determined by ether-extraction and Babcock methods. Protein was determined by the Kjeldahl method. The percent lean is simply the difference between the percent fat and 100%.

Results are given in Table 1 for samples weighing over 2000 pounds and in Table 2 for samples weighing less than 2000 pounds. The relationship between the net counting rates and the percents of lean given in Table 1 was analyzed by the following least squares fitting routine (written in BASIC), where a data point is the coordinate defined by the net counting rate X in counts per 200 sec. and the percent by weight of lean Y:

| Line | Statement/Command |
|---|---|
| 10 | J=0;K=0;L=0;M=0;G=0 |
| 15 | INPUT "NUMBER OF DATA POINTS"; N |
| 20 | FOR I=1 TO N |
| 25 | INPUT "ENTER POINT COORDINATE, X,Y"; X,Y |
| 30 | J=J+X;K=K+Y;L=L+X*X;M=M+X*Y;G=G+Y*Y |
| 35 | NEXT I |
| 40 | B=J/N |
| 45 | S=(B*K−M)/(B*J−L) |
| 50 | I=(K−J*S)/N |
| 55 | PRINT "EQUATION IS; LEAN,%W=" I "+" S "*NET COUNT RATE" |

The regression line computed from data given in Table 1 is as follows:

$$Y_{lean} = f(x) = 0.11776X + 13.5286 \qquad (1)$$

The standard deviation of the observed lean values from the line of Equation (1) is 3.8% relative. Analysis of the relationship between net counts per 200 sec. (X) and the percent by weight of protein (Y) using the data in Table 1 and the above fitting routine gives the following regression line:

$$Y_{protein} = f(x) = 0.02465X + 2.5735 \qquad (2)$$

The standard deviation of the observed protein values from the line of Equation (2) is 2.9% relative.

The function generator 52 may be programmed to generate either or both of the functions of Equations (1) and (2) for the particular system used.

The samples that weighed under 2000 pounds did not shield the detector from background radiation as effectively as did the heavier samples. Therefore, the first step in interpreting the data from Table 2 was to correct the background values for this effect. This was done by using the lean values obtained by laboratory analysis in conjunction with Equation (1) to calculate the expected net counting rates. The calculated net count rates were subtracted from the gross count rates (Table 2) to obtain the corrected background count rates (B2). A ratio, R, defined as the corrected background (B2) divided by the observed background (B1), was calculated. These steps are summarized in Table 3.

The regression line relationship between sample weight W in pounds and the ratio R was obtained by least squares fitting, and is as follows:

$$R = -0.0005451W + 2.1083 \qquad (3)$$

The function generator 54 may be programmed to generate this function.

The corrected background for samples that weigh under 2000 lb. can then be obtained from the correction circuit 56 by multiplying the observed background by the ratio R which is computed from the sample weight by Equation (3). As can be seen by the analysis of data from samples that weigh over 2000 lb., background correction was not necessary for such samples.

Figure 4:
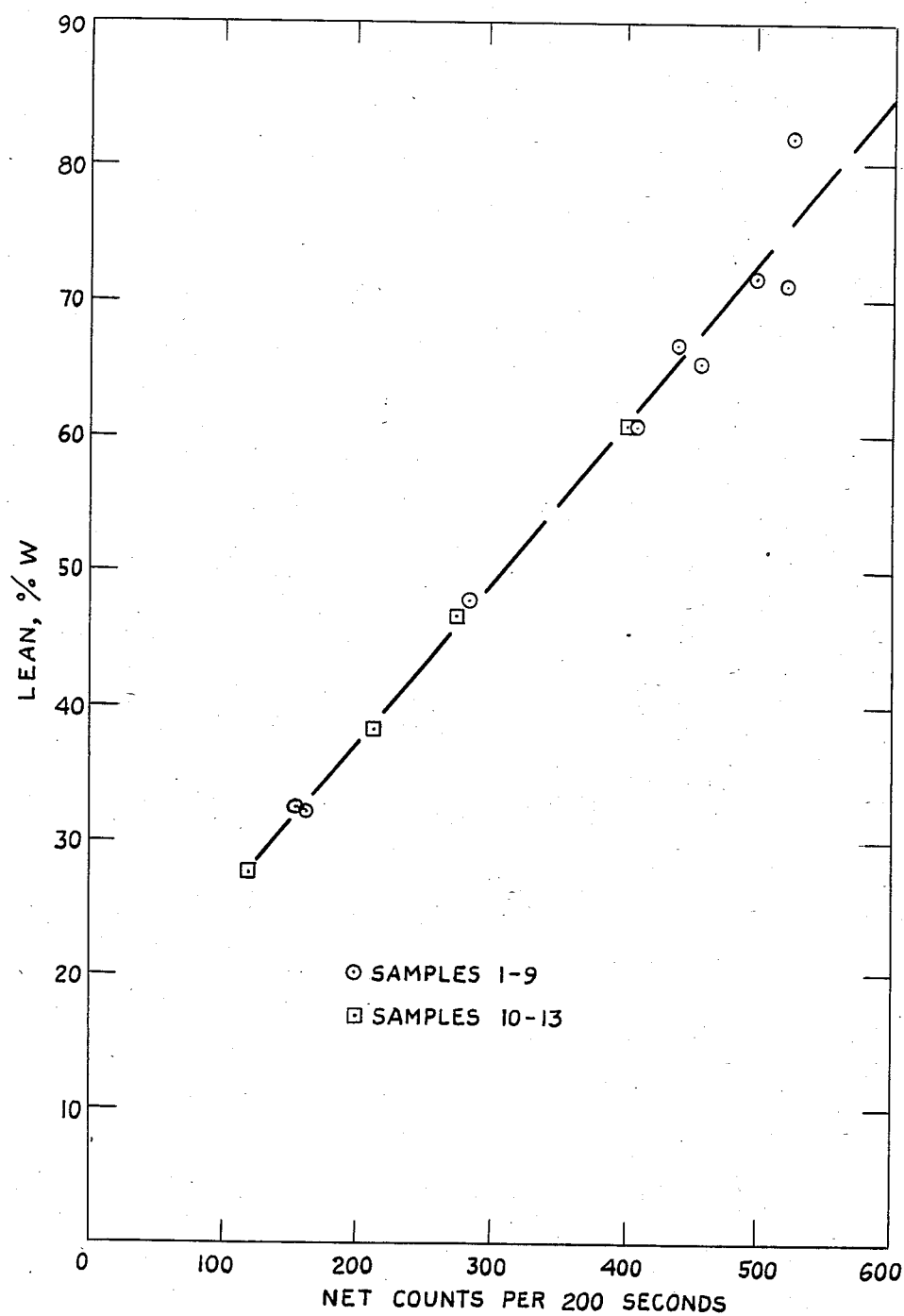
FIG. 4 is a graphic illustration of the relationship between net counting rate and percent by weight (% w) of lean meat as determined by the system shown in FIG. 1.

To illustrate the procedure for correcting the background for lightweight samples, and the quality of the results that follow from the procedure, the data in Table 2 were analyzed. The values of R for each of the four samples were calculated using Equation (3), and the corrected background values were obtained by multiplying the observed background values by R for each sample. The net counts were obtained by subtracting the corrected background counts from the gross counts, and the lean values were calculated using Equation (1). The procedure and the results are summarized in Table 4. All 13 data points, including the four corrected data points for lightweight samples are plotted in FIG. 4.

The foregoing experimental data were obtained in a meat processing plant utilizing the equipment and procedures set forth above. The results of the work demonstrate that the equipment and procedures can successfully measure lean, fat, and/or protein is large quantities of meat. As these data show, at least over limited ranges straight line approximations made by least squares approximation have proven suitably accurate. Other approximations and interpolations may be used, as desired. In particular, as mentioned above, the functions of the function generator 52 may include accounting for weight differences.

Other modifications may also be made within the scope of the invention. For example, a plurality of probes 13 (notably two) may be used in parallel to provide greater sensitivity. When embedded at different locations in the meat while still adequately shielded by the meat, the multiple probes average out inhomogeneities in the sample to some degree. It is also within the invention to insert the same probe at two different locations, making separate measurements and combining them.

In determining background, the same counting circuit can be used for both background and sample counting rates. In any event, the background counting rate signal is stored for application to the difference circuit 48, or it may be entered in the correction circuit or the difference circuit and stored there.

The particular embodiment described is simply a particular mode that has been developed and proven satisfactory.

TABLE 1

Measurements of Nine Samples of Pork Over 2000 lb.

| Sample No. | Weight, lb. | Analysis, % w | | | Counts/200 sec. | | |
|---|---|---|---|---|---|---|---|
| | | Fat | Lean | Protein | Sample | Bkgd. | Net |
| 1 | 2015 | 67.4 | 32.6 | 6.5 | 1196 | 1036 | 160 |
| 2 | 2280 | 29.0 | 71.0 | 15.3 | 1559 | 1036 | 523 |
| 3 | 2153 | 67.5 | 32.5 | 6.6 | 1198 | 1036 | 162 |
| 4 | 2235 | 33.2 | 66.8 | 13.5 | 1479 | 1036 | 443 |
| 5 | 2235 | 34.6 | 65.4 | 13.4 | 1486 | 1026 | 460 |
| 6 | 2231 | 18.2 | 81.8 | 16.5 | 1552 | 1026 | 526 |
| 7 | 2148 | 52.3 | 47.7 | 9.7 | 1310 | 1026 | 284 |
| 8 | 2114 | 39.2 | 60.8 | 12.8 | 1437 | 1026 | 411 |
| 9 | 2250 | 28.2 | 71.8 | 14.4 | 1492 | 991 | 501 |

TABLE 2

Measurements of Four Samples of Pork under 2000 lb.

| Sample No. | Weight, lb. | Analysis, % w | | Counts/200 sec. | |
|---|---|---|---|---|---|
| | | Fat | Lean | Sample | Bkgd. |
| 10 | 1485 | 61.5 | 38.5 | 1545 | 1026 |
| 11 | 1875 | 72.4 | 27.6 | 1197 | 991 |
| 12 | 1913 | 53.4 | 46.6 | 1369 | 1026 |
| 13 | 1950 | 39.2 | 60.8 | 1441 | 991 |

TABLE 3

Corrected Background and the Ratio R

| Sample No. | Weight, lb. | Counts/200s Sample | Net (Eq. 1) | Bkgd. Counts/200s Corr. B2 | Obs. B1 | Ratio R B2/B1 |
|---|---|---|---|---|---|---|
| 10 | 1485 | 1545 | 212 | 1333 | 1026 | 1.299 |
| 11 | 1875 | 1197 | 119 | 1078 | 991 | 1.088 |
| 12 | 1913 | 1369 | 281 | 1088 | 1026 | 1.060 |
| 13 | 1950 | 1441 | 401 | 1040 | 991 | 1.049 |

TABLE 4

Calculated Lean Values for Samples Under 2000 lb.

| Sample No. | Wt. lb. | Ratio (Eq. 3) | Bkgd. Obs. | C/200s Corr. | Sample C/200s | Net C/200s | Lean, (Eq. 1) | % w Anal. |
|---|---|---|---|---|---|---|---|---|
| 10 | 1485 | 1.299 | 1026 | 1332 | 1545 | 213 | 38.6 | 38.5 |
| 11 | 1875 | 1.086 | 991 | 1076 | 1197 | 121 | 27.8 | 27.6 |
| 12 | 1913 | 1.066 | 1026 | 1093 | 1369 | 276 | 46.0 | 46.6 |
| 13 | 1950 | 1.045 | 991 | 1036 | 1441 | 405 | 61.2 | 60.8 |

What is claimed is:

1. A meat grader for grading a meat sample disposed in a bin of predetermined dimensions wherein said meat sample extends at least about two feet in all directions, said meat grader comprising:

at least one probe including a housing containing a scintillation phosphor responsive to gamma rays including 1.46 Mev gamma rays from potassium-40 for producing corresponding light pulses of magnitude systematically related to the energy of the incident gamma rays, and photomultiplier means optically coupled to said phosphor and responsive to said light pulses for producing corresponding electronic pulses of magnitude systematically related to the magnitude of said light pulses, said probe being adapted to penetrate said meat sample in said bin to dispose said phosphor near the center of said meat sample at least about a foot from the margin thereof, differential pulse height discrimination means coupled to the output of said photomultiplier means for selectively responding to such of said electronic pulses as are of a limited range of magnitude including that characteristic of such pulses occasioned by the incidence of said 1.46 Mev gamma rays upon the respective said phosphor by producing corresponding' discriminated signal pulses, counting rate means responsive to said discriminated signal pulses for counting the number of said discriminated signal pulses in a predetermined time interval to provide a gross counting rate signal corresponding to gross counting rate, background counting rate means for providing a background counting rate signal corresponding to the number of discriminated signal pulses in said predetermined period of time occurring with said at least one probe in an environment corresponding to the meat sample in the absence of potassium-40, and differential means responsive to said background counting rate signal and said gross counting rate signal for producing a net counting rate signal corresponding to the difference between said gross counting rate and said background counting rate is a net counting rate corresponding to 1.46 Mev gamma rays from potassium-40.

2. A meat grader according to claim 1 wherein there are at least two said probes.

3. A meat grader according to claim 1 wherein said probe includes a pointed end for penetrating said meat.

4. A meat grader according to claim 1 wherein said background counting rate means includes means responsive to a signal corresponding to the weight of said meat sample for correcting the background count signal for nonstandard weight of said sample.

5. A meat grader according to claim 1 further including indicating means systematically responsive to said net counting rate signal for indicating the relative leanness or protein content of said meat sample.

6. A meat grader according to claim 5 wherein said background counting rate means includes means responsive to a signal corresponding to the weight of said meat sample for correcting the background count signal for nonstandard weight of said sample.

7. A meat grader according to claim 5 wherein said indicating means includes means responsive to a signal corresponding to the weight of said meat sample for controlling said systematic response to said net counting rate signal.

8. A meat grader according to claim 6 wherein said indicating means includes means responsive to a signal corresponding to the weight of said meat sample for controlling said systematic response to said net counting rate signal.

9. A meat grader according to claim 1 further including a container containing a predetermined volume of water for producing said environment corresponding to the meat sample in the absence of potassium-40.

10. A method of grading meat comprising:

disposing a meat sample in a bin of predetermined dimensions wherein said meat extends at least about two feet in all directions, inserting into said meat sample at least one probe including a housing containing a scintillation phosphor responsive to gamma rays including 1.46 Mev gamma rays from potassium-40 for producing corresponding light pulses of magnitude systematically related to the energy of the incident gamma rays, and a photomultiplier optically coupled to said phosphor and responsive to said light pulses for producing corresponding electronic pulses of magnitude systematically related to the magnitude of said light pulses, said probe being inserted into said meat in said bin to dispose said phosphor near the center of said meat at least about a foot from the margin thereof, selectively detecting such of said electronic pulses as are of a limited range of magnitude including that characteristic of such pulses occasioned by the incidence of said 1.46 Mev gamma rays upon a said phosphor by producing corresponding discriminated signal pulses, counting the number of said discriminated signal pulses in a predetermined time interval while said probe is disposed in said sample to provide a gross counting rate, providing a background counting rate corresponding to the number of said discriminated signal pulses in said predetermined period of time while said at least one probe is in an environment corresponding to the meat sample in the absence of potassium-40, and subtracting said background count from said gross counting rate to produce a net counting rate corresponding to 1.46 Mev gamma rays from potassium-40.

11. A method according to claim 10 wherein a probe is inserted in at least two places in said sample.

12. A method according to claim 10 wherein said background counting rate is corrected for nonstandard weight of said sample before subtracting it from said gross counting rate.

13. A method according to claim 10 further including converting said net counting rate into an indication of the relative leanness or protein content of said meat sample.

14. A method according to claim 13 further including correcting the net counting rate for nonstandard weight of said sample.

15. A method according to claim 13 further including modifying said converting to adjust for nonstandard weight of said sample.

16. A method according to claim 10 wherein said step of providing a background counting rate includes disposing said at least one probe in a container containing a predetermined volume of water to provide said environment corresponding to the meat sample in the absence of potassium-40.

* * * * *

UNITED STATES PATENT AND TRADEMARK OFFICE
CERTIFICATE OF CORRECTION

PATENT NO. : 4,590,377
DATED : May 20, 1986
INVENTOR(S) : H. Richard Lukens

It is certified that error appears in the above-identified patent and that said Letters Patent is hereby corrected as shown below:

Column 3, line 66, change "on" to --an--.

Column 6, line 19, change "acount" to --account--.

Column 6, line 34, after "below" insert a period.

Column 8, line 14, change "is" to --in--.

Column 8, line 35, change "sampIe" to --sample--.

Column 9, line 48, Claim 1, delete the apostrophe after "corresponding".

Column 9, line 64, Claim 1, change "is" to --as--.

Signed and Sealed this

Twenty-third Day of September 1986

[SEAL]

Attest:

DONALD J. QUIGG

Attesting Officer

Commissioner of Patents and Trademarks